US008600476B2

(12) United States Patent
Bi et al.

(10) Patent No.: US 8,600,476 B2
(45) Date of Patent: Dec. 3, 2013

(54) PATIENT SUPPORT TABLE CONTROL SYSTEM FOR USE IN MR IMAGING

(75) Inventors: Xiaoming Bi, Aurora, IL (US);
Christopher Glielmi, Chicago, IL (US);
Peter Schmitt, Weisendorf (DE); Peter Weale, Worcester (GB); Michael Zenge, Nürnberg (DE); Sven Zuehlsdorff, Chicago, IL (US)

(73) Assignee: Siemens Aktiengesellschaft, Munich (DE)

( * ) Notice: Subject to any disclaimer, the term of this patent is extended or adjusted under 35 U.S.C. 154(b) by 49 days.

(21) Appl. No.: 13/281,743

(22) Filed: Oct. 26, 2011

(65) Prior Publication Data

US 2012/0271156 A1  Oct. 25, 2012

Related U.S. Application Data

(60) Provisional application No. 61/477,701, filed on Apr. 21, 2011.

(51) Int. Cl.
*A61B 5/05* (2006.01)

(52) U.S. Cl.
USPC .......................................... 600/415; 600/410

(58) Field of Classification Search
USPC ................................. 600/407–429
See application file for complete search history.

(56) References Cited

U.S. PATENT DOCUMENTS

| 6,912,415 | B2 | 6/2005 | Kruger et al. | |
| 7,251,520 | B2 | 7/2007 | Shankaranarayannan et al. | |
| 7,522,744 | B2 * | 4/2009 | Bai et al. | 382/100 |
| 7,610,076 | B2 * | 10/2009 | Riederer et al. | 600/415 |
| 2003/0216637 | A1 * | 11/2003 | Ho et al. | 600/415 |
| 2005/0171423 | A1 * | 8/2005 | Ho et al. | 600/410 |
| 2007/0222442 | A1 | 9/2007 | Aldefeld et al. | |
| 2009/0177076 | A1 * | 7/2009 | Aldefeld et al. | 600/410 |
| 2011/0112392 | A1 | 5/2011 | Boernert et al. | |
| 2011/0184273 | A1 | 7/2011 | Riederer | |

OTHER PUBLICATIONS

D.G. Kruger, et al., "A dual-velocity acquisition method for continuously-moving-table contrast-enhanced MRA", Proc. Intl. Soc. Mag. Reson. Med. 11 (2004).
H.-P. Fautz, "Sliding Multislice (SMS): A New Technique for Minimum FOV Usage in Axial Continuously Moving-Table Acquisitions" Magnetic Resonance in Medicine 55: 363-370 (2006).
Jorg Barkhausen, et al., "Whole-Body MR Imaging in 30 Seconds with Real-Time True FISP and a Continuously Rolling Table Platform: Feasibility Study", Whole Body MR Imaging with Real-Time True FISP, vol. 220, No. 1, Radiology, Jul. 2001.

(Continued)

*Primary Examiner* — Sanjay Cattungal
(74) *Attorney, Agent, or Firm* — Joshua B Ryan

(57) ABSTRACT

A system for Non-Contrast Agent enhanced MR imaging includes an MR image acquisition device for acquiring imaging datasets comprising one or more image slabs individually comprising multiple image slices. An image data processor processes data representing an acquired image slice to detect a predetermined anatomical feature of a patient by detecting an edge of the anatomical feature in response to detection of pixel luminance transitions. A patient support table controller automatically moves a patient table at a velocity adaptively and dynamically determined by, selecting data modifying table velocity from predetermined information associating an anatomical feature with table velocity modification data in response to detection of the anatomical feature and adaptively determining a table velocity using the modification data.

20 Claims, 8 Drawing Sheets

(56) References Cited

OTHER PUBLICATIONS

Peter Bornert, PhD and Bernd Aldefeld, PhD, "Principles of Whole-Body Continuously-Moving-Table MRI", Journal of Magnetic Resonance Imaging 28:1-12 (2008).

M.O. Zenge, et al., "Quiescent-Interval Single-Shot Unenhanced Magnetic Resonance Angiogrphay featuring Continuous Table Movement", MR Applications Development, Siemens AG, Erlangen, Germany, Cardiovascular MR R&D, Siemens Helathcare, Chicago, IL, United States, Department of Radiology, NorthShore University HealthSystem Evanston, IL, United States.

* cited by examiner

FIGURE 6

| Feature Detected | Extent of Feature | | | |
|---|---|---|---|---|
| | Very Significant | Significant | Moderate | Slight |
| Flow Reduction | 0.5 | 0.6 | 0.7 | 0.8 |
| Artifact | 0.6 | 0.7 | 0.8 | 0.9 |
| Heart Deformation | 0.4 | 0.6 | 0.8 | 1.0 |
| Tumor | 0.3 | 0.6 | 0.8 | 0.9 |
| External Device | 0.3 | 0.4 | 0.6 | 0.8 |
| ... | ... | ... | ... | ... |

| | ΔVelocity Proportion |
|---|---|
| Flow Reduction | 0.7 |
| Artifact | 0.6 |
| Heart Deformation | 0.5 |
| Tumor | 0.3 |
| External Device | 0.4 |
| ⋮ | ⋮ |

…

PATIENT SUPPORT TABLE CONTROL SYSTEM FOR USE IN MR IMAGING

This is a non-provisional application of provisional application Ser. No. 61/477,701 filed 21 Apr., 2011, by C. Glielmi et al.

FIELD OF THE INVENTION

This invention concerns a system for Non-Contrast Agent enhanced MR imaging involving automatically moving a patient table at a velocity adaptively and dynamically determined using information associating an anatomical feature with table velocity modification data.

BACKGROUND OF THE INVENTION

In magnetic resonance imaging (MRI), continuous table movement MRI enables fast imaging at isocenter for improved image quality that maintains continuity through patient support table movement direction and extends imaging field of view. Aspects affecting MRI imaging include (i) proximity to magnet isocenter (the most homogenous imaging region) and (ii) shimming of a main magnetic field to maximize field homogeneity and resultant image quality. Image acquisition in known systems is typically conducted by use of a static patient support table or by continuous table movement at constant table velocity throughout image acquisition. A static patient table without table movement during acquisition is common where images are acquired in a relatively localized region. For image scans involving large imaging regions (whole body, peripheral extremities, spine, for example), a table is moved between scans (while no data is acquired) followed by shimming at the new table position before image acquisition is resumed. Limitations of the known method include limited FOV (i.e., (Field of View—imaged anatomical area) for a given table position, potential image degradation at the edges of the FOV for image regions farther from isocenter, and discontinuities at the edges of image regions that are combined for viewing and diagnosis. Furthermore, performing needed separate magnetic field shimming operations at each table position is time consuming.

The use of continuous table movement during imaging allows for constant imaging near isocenter resulting in image quality improvement. Furthermore, shimming is more efficient and hence less time consuming. Additionally, continuous table movement acquisition provides image quality continuity throughout an extended FOV because separate scans at different static table positions are not needed. However, a single table velocity might not be optimal for different regions of the imaging FOV as anatomy and physiology can vary throughout the body. One known system described by Kruger G, et al. in a paper entitled "A dual-velocity acquisition method for continuously-moving-table contrast-enhanced MRA", Proc ISMRM 2004, p. 233, utilizes a dual velocity approach to account for reduced flow in peripheral regions for contrast enhanced magnetic resonance angiography. This method utilizes a higher table velocity during data acquisition in the torso and reduced table velocity as the FOV reaches the knees. Another known system described by Aldefeld B, Boernert P, Kuepp J, et al. in a patent Application entitled "MRI of a continuously moving object involving motion compensation, US2009/0177076A1, Jul. 9, 2009, detects patient motion (including respiratory or cardiac gating variability) to modify table velocity during continuous table movement MRI. A system according to invention principles addresses the deficiencies and problems of these and other known systems.

SUMMARY OF THE INVENTION

A system varies table speed during continuous table movement magnetic resonance imaging (MRI) acquisition in response to imaging features detected from a previous scan and data-driven feedback based on imaging features during the current scan, for imaging different body regions for a variety of image acquisition, pulse sequences. A system for Non-Contrast Agent enhanced MR imaging includes an MR image acquisition device for acquiring imaging datasets comprising one or more image slabs individually comprising multiple image slices. An image data processor processes data representing an acquired image slice to detect a predetermined anatomical feature of a patient by detecting an edge of the anatomical feature in response to detection of pixel luminance transitions. A patient support table controller automatically moves a patient table at a velocity adaptively and dynamically determined by, selecting data modifying table velocity from predetermined information associating an anatomical feature with table velocity modification data in response to detection of the anatomical feature and adaptively determining a table velocity using the modification data.

BRIEF DESCRIPTION OF THE DRAWING

FIG. 6 shows a further lookup table, associating multiple values of severity of anatomical characteristics of anatomical features (flow reduction, artifact, heart deformation, tumor, external device) with table velocity modification data, according to invention principles.

DETAILED DESCRIPTION OF THE INVENTION

A system varies table speed during continuous table movement magnetic resonance imaging (MRI) acquisition based on imaging features detected from a previous scan and data-driven feedback based on imaging features during the current scan. The system is applicable for imaging different body regions for a variety of image acquisition pulse sequences. The inventors have advantageously recognized that continuous table movement at constant table velocity throughout image acquisition employed by known systems may impair imaging quality particularly for cardiac-gated acquisition, when heart-rate variability leads to inconsistent image acquisition timing. The inventors have further advantageously recognized MR imaging of varying anatomical portions may be improved by use of anatomical region-specific table speed. A system utilizes image-based feedback during image acquisition (and/or a previous scan) to modify table velocity during image acquisition for optimal image quality. The continuous table movement system is compatible with various pulse sequences and is applicable to different body regions.

Optimal MR acquisition is dependent on a variety of factors that may change over the course of imaging a Field of View (FOV—imaged anatomical area). The system advantageously modifies table velocity in response to multiple different region-specific acquisition parameters. Known systems teach using a slower velocity for imaging a lower peripheral anatomic region (e.g. a limb) using contrast agent enhanced MRA (Magnetic Resonance Angiography). In contrast, the system adaptively changes table velocity in response to image-based features by determining multiple velocities in response to image features from a previous scan of the same patient and/or by real-time data-driven feedback using table velocity calculated in response to imaging features detected during current image acquisition.

Figure 1:
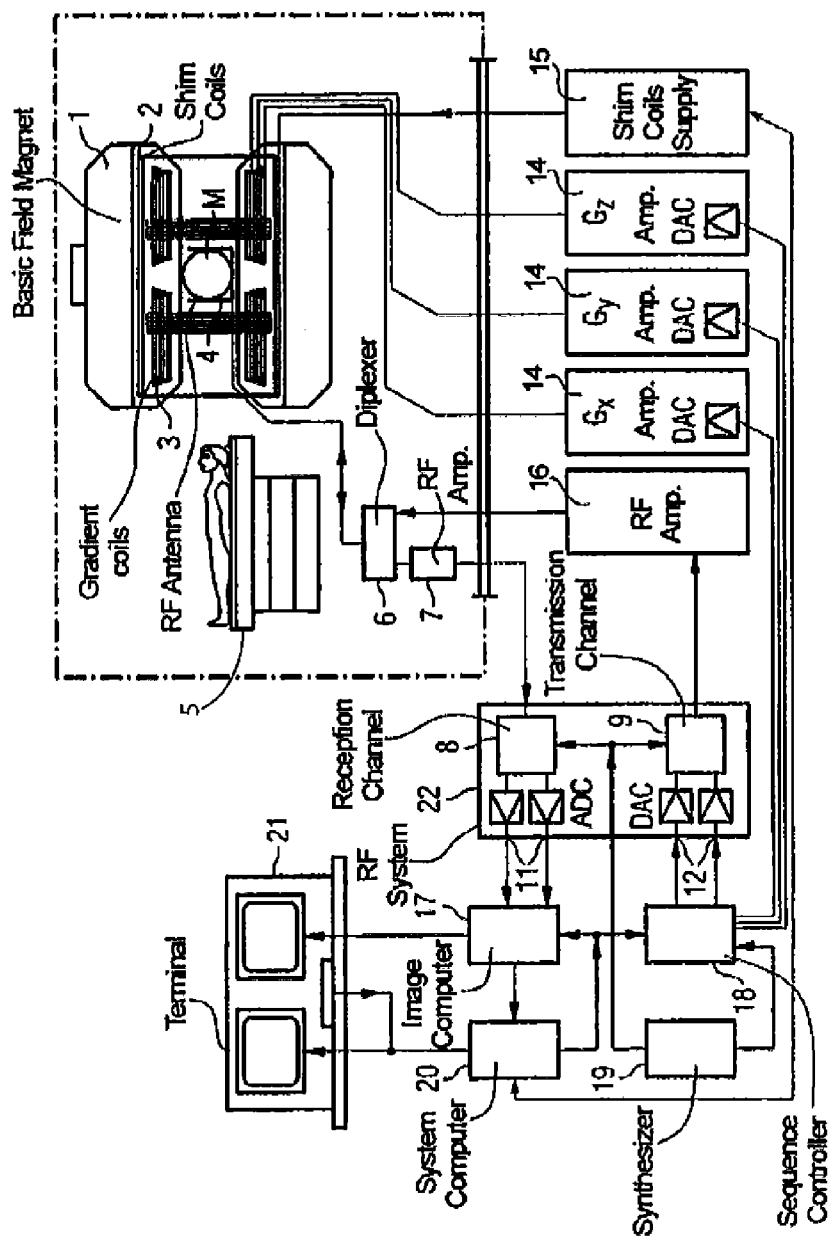
FIG. 1 shows a system for Non-Contrast Agent enhanced MR imaging, according to invention principles.

FIG. 1 shows a schematic block diagram of MR imaging system 10 for Non-Contrast Agent enhanced MR imaging. A basic field magnet 1 generates a strong magnetic field, which is constant in time, for the polarization or alignment of the nuclear spins in the examination region of an object, such as, for example, a part of a human body to be examined on automated movable patient support table 5. The automated patient support table 5 is controlled by system computer 20. The high homogeneity of the basic magnetic field required for the magnetic resonance measurement is provided in a spherical measurement volume M, for example, into which the parts of the human body to be examined are brought. In order to satisfy the homogeneity requirements and especially for the elimination of time-invariant influences, shim-plates made of ferromagnetic material are mounted at suitable positions. Time-variable influences are eliminated by shim coils 2, which are controlled by a shim-current supply 15.

Imaging computer 17 reconstructs an image from processed acquired RF echo pulse data. The processing of RF data, the image data and the control programs is performed under control of system computer 20. In response to predetermined pulse sequence control programs, sequence controller 18 controls generation of desired pulse sequences and corresponding scanning of k-space. In particular, sequence controller 18 controls the switching of the magnetic gradients at appropriate times, transmission of RF pulses with a determined phase and amplitude and reception of magnetic resonance signals in the form of RF echo data. Synthesizer 19 determines timing of operations of RF system 22 and sequence controller 18. The selection of appropriate control programs for generating an MR image and the display of the generated nuclear spin image is performed by a user via terminal (console) 21, which contains a keyboard and one or more screens.

The system 10 MR image acquisition device acquires imaging datasets comprising one or more image slabs individually comprising multiple image slices. An image data processor (in imaging computer 17) processes data representing an acquired image slice to detect a predetermined anatomical feature of a patient by detecting an edge of the anatomical feature in response to detection of pixel luminance transitions. A patient support table controller (in system computer 20) automatically moves patient table 5 at a velocity adaptively and dynamically determined by, selecting data modifying table velocity from predetermined information associating an anatomical feature with table velocity modification data in response to detection of the anatomical feature and adaptively determines a table velocity using the modification data.

Optimal patient table velocity is dependent on a number of attributes, some of which are detected using real-time feedback due to unpredictability of events. System computer 20 advantageously modifies table velocity in a real-time manner based on imaging features including, detected localized vessel anatomy (e.g. aortic bifurcation or peripheral trifurcation) and/or anomalies (e.g. aneurism and stenosis, for example), detected congenital heart disease (e.g. unexpected anatomy, vascular ring) and additional functional measurements at different FOV positions (e.g. flow along different locations of the ascending/descending aorta). System computer 20 also modifies table velocity in a real-time manner based on detected pathology (e.g. tumors and other masses, aneurisms), detected regions of artifacts (e.g. metal artifacts that could be reduced by using different imaging parameters within this region), detected regions of altered physiology (e.g. slow flow for flow-dependent techniques) and detected localized devices (e.g. sternal wires). In response to detected image features, system computer 20 adaptively alters patient table 5 velocity and may reverse table direction (e.g. reverse flow, repeating a FOV section, in response to a missed trigger) and adapts size of a 3D acquisition slab. The system advantageously utilizes data-driven, patient specific image attributes to modify table velocity based on image features and determines dynamic table velocity.

Figure 2:
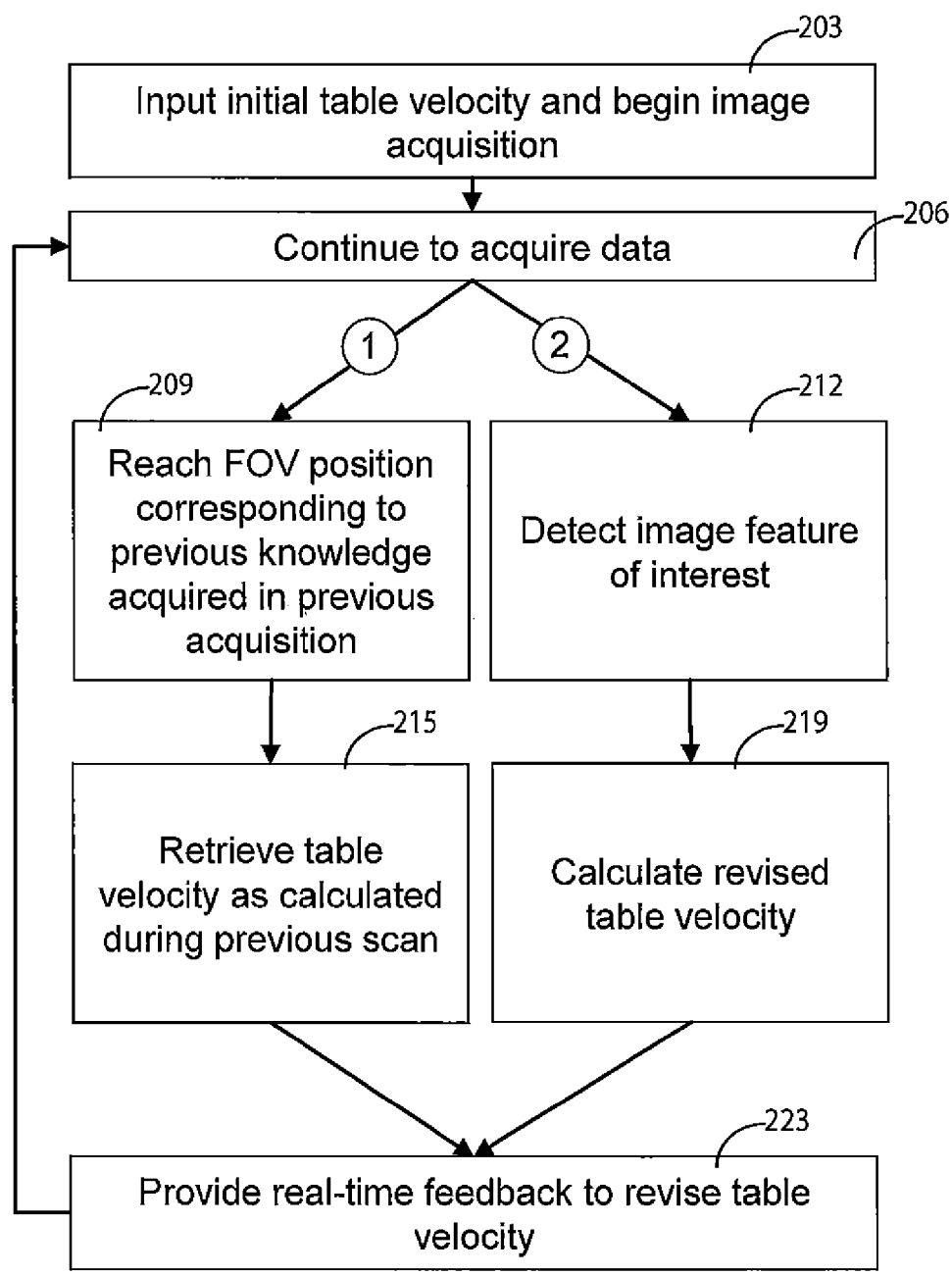
FIG. 2 shows a flowchart of a process for continuous table movement magnetic resonance image acquisition in response to an anatomical feature detected in an image acquired in a previous scan and/or real time modification of table velocity data in response to an anatomical feature detected in an image acquired in a current scan or a detected physiological event occurring during the current scan, according to invention principles.

FIG. 2 shows a flowchart of a process performed by system 10 (FIG. 1) for continuous table movement magnetic resonance image acquisition in response to an anatomical feature detected in an image acquired in a previous scan and/or real time modification of table velocity data in response to an anatomical feature detected in an image acquired in a current scan or a detected physiological event occurring during the current scan. System 10 determines table velocities based on previous scans. In step 203 a patient support table controller acquires an initial table velocity value and the system 10 MR image acquisition device initiates image acquisition and continues image acquisition during table movement in step 206. In step 209 the image data processor utilizes images acquired during previous scans of the same patient to determine table velocities for various FOV sections of the patient to be imaged. The image data processor analyzes images acquired during the initial imaging scan to automatically identify and classify different anatomical regions. Table velocity determination (modification) data is determined as a function of FOV position from predetermined information associating an anatomical feature with table velocity modification data in response to detection of an anatomical feature. Subsequently, FOV-specific table velocities are retrieved in step 215 by the processor from the predetermined information when a continuous table movement scan is prepared and table velocity (as well as other imaging parameters) are used based on spatial position within the imaging FOV.

Alternatively to step 209 (or in parallel with step 209), in step 212, the image data processor utilizes real-time feedback to modify table velocity. Specifically in step 212, in response to the imaging processor detecting an anatomic feature in an image acquired in a current scan, a revised table velocity is calculated and executed in step 219. The image data processor advantageously reacts to patient-specific and unpredictable image features and acquires optimized data without a localized prescan. The image data processor in step 223, adaptively dynamically automatically determines a table velocity value and time of application of the value from a lookup table associating image features with table velocity modification data. The system updates table velocity throughout an imaging scan to improve image quality in response to detected anatomical or physiological changes throughout a FOV.

System 10 is usable in multiple different applications including in two dimensional (2D) non-contrast MRA in which axial slices are acquired in an ascending fashion during table movement where vessel size and orientation dictate optimal slice thickness and distribution (i.e. overlap) in the head-foot direction. Vessels at a vessel trifurcation point are typically not orthogonal to slice acquisition; therefore, to minimize partial volume effects, thinner slices with slice overlap reduce partial volume effects. This advantage can exceed the decreased signal to noise ratio (SNR) associated with such imaging protocol modifications.

Figure 3:
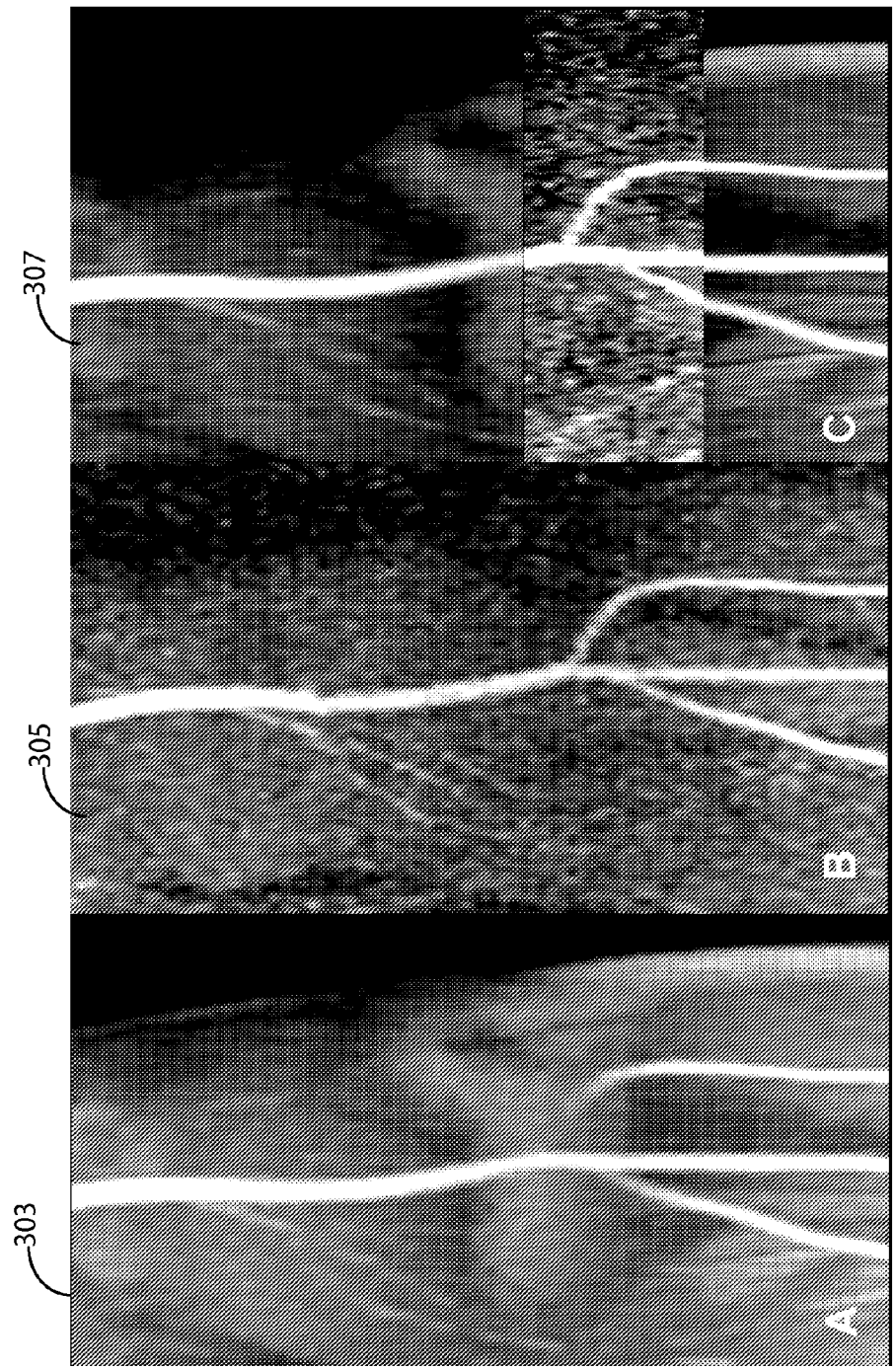
FIG. 3 shows comparison of images acquired by known systems and a continuous table movement system according to invention principles.

FIG. 3 shows comparison of images 303, 305 acquired by known systems and image 307 acquired using system 10 including the continuous table movement system. Image 303 is acquired using standard continuous table movement at constant standard velocity, standard slice thickness (3 mm) and RF excitation pulse properties and shows blurring at the vessel trifurcation point. The blurring is improved by use of a constant but slower table speed due to thinner slices (2.3 mm) with slice overlap and longer RF pulses for improved slice profile as illustrated in image 305. Imaging system 10 acquires image 307 using a combination of these acquisitions depending on local anatomical features that adaptively varies table velocity depending on local anatomical features such as vessel orientation. Larger vessels that are orthogonal to an imaging slice are best depicted with thicker slices and higher table velocity while the trifurcation, which includes vessels that are oblique to imaging slice, are best depicted with thinner slices and reduced table velocity. System 10 uses computer 20 in automatically moving patient table 5 at a velocity adaptively and dynamically determined by, selecting data modifying table velocity from predetermined information associating an anatomical feature (the vessel trifurcation) with table velocity modification data in response to detection of the vessel trifurcation and adaptively determines a table velocity using the modification data. Thereby system 10 acquires image 307 comprising an optimal result.

Although this example utilizes two separate acquisitions with different, constant table velocities, it demonstrates that table velocities optimized for different FOV sections may improve image quality. Real-time image analysis is used to detect smaller arteries that are not orthogonal to the imaging plane and provide feedback to reduce table velocity and slice thickness. In response to vessel trifurcation detection, subsequent detection of larger vessels that are orthogonal to an imaging plane may trigger increased table velocity and slice thickness. System 10 advantageously uses variable table velocity (as well as other imaging parameters such as slice thickness) adaptively determined before or during a continuous table movement scan based on image features. This system is usable in various continuous table movement acquisitions, including but not limited to angiography, oncological examinations and spinal imaging. The system provides continuous table movement for Magnetic Resonance Imaging with variable table velocity to optimize acquisition for anatomical region-specific attributes.

Figure 4:
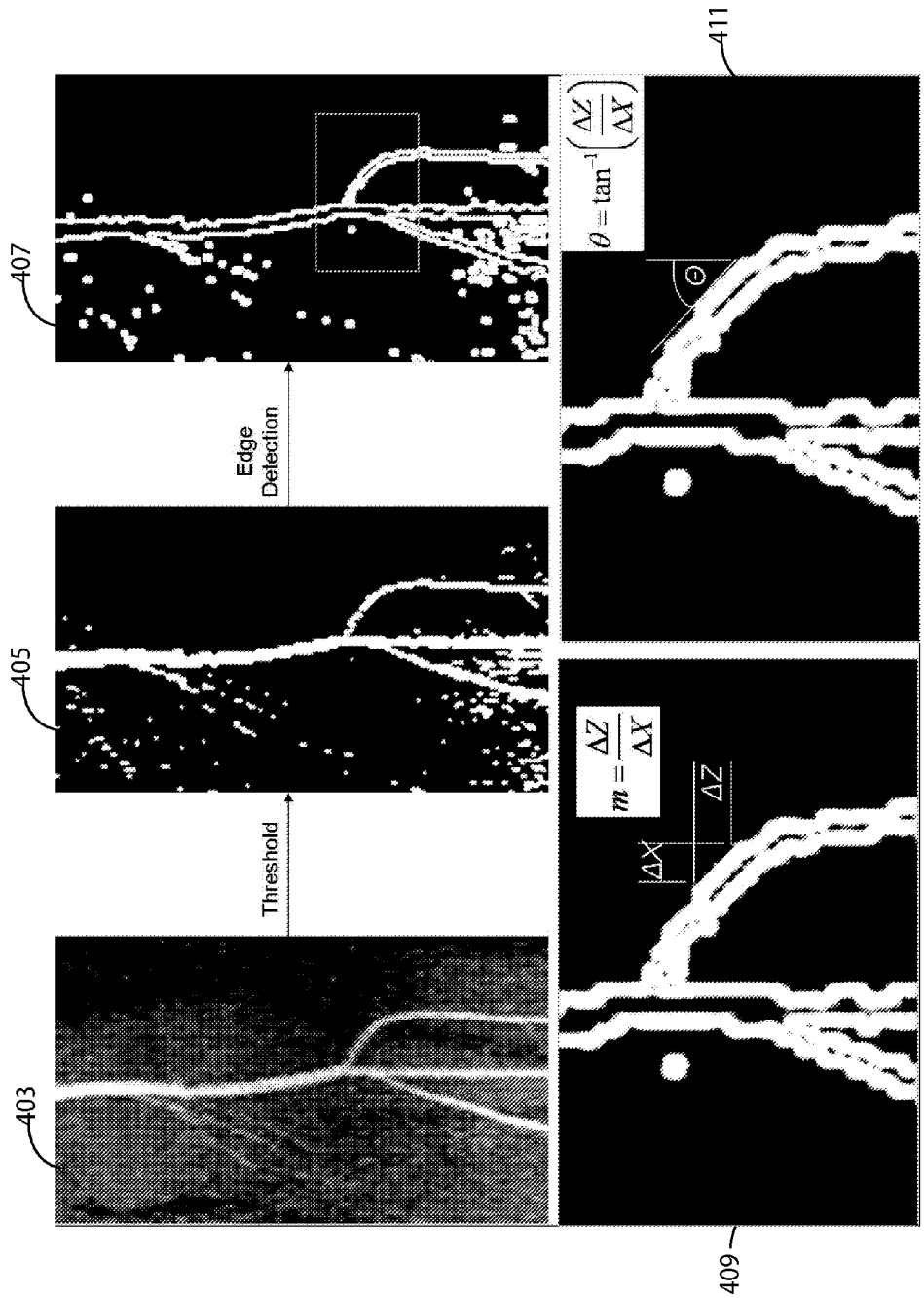
FIG. 4 shows anatomical feature detection in an image acquired in a scan that is used for table movement modification, according to invention principles.

FIG. 4 illustrates anatomical feature detection in an image acquired in a scan that is used for table movement modification. Initial table velocity ($V_I$) is determined using a priori assumptions based on the type of imaging examination concerned, age, and suspected clinical pathology. During image acquisition, table velocity (V) is modified as a function of position along the direction of table movement (z) based on detected image features. An imaging scan type has one or several corresponding anatomical features of interest that if detected lead to a table velocity modification. An individual imaging slice (for 2D imaging) or imaging slab (for 3D imaging) is reconstructed and analyzed in the image domain for particular anatomical features.

The image data processor processes data representing an acquired image slice to detect a predetermined anatomical feature of a patient by detecting an edge of the anatomical feature in response to detection of pixel luminance transitions. The processor calculates maximum intensity projection in anterior-posterior direction and performs a histogram analysis to determine a pixel luminance threshold value that indicates pixels comprising a vessel. In the histogram, a horizontal axis represents each possible luminance pixel value from black to white. The vertical axis indicates values representing the number of pixels in the image that occur at each luminance pixel value level. The processor applies the determined threshold to image representative pixel luminance data of image 403 to identify vessels as illustrated in image 405 and determines vessel orientation. The processor employs an edge detection function to determine a boundary of a feature (e.g. vessel) by determining a transition in pixel luminance values as illustrated in image 407.

The image data processor performs a slope calculation of vessel edges in a given sub-region or slice as a function of z coordinates as shown in image 409. Specifically, for an increment in the z direction ($\Delta Z$), the processor determines slope (m) as the ratio $\Delta Z$ over $\Delta X$ for a given edge. Further, for each edge (image 409 has 4 edges in a calculation plane), the processor determines the angle ($\Theta$) as the inverse tangent of the slope ($\Theta=0$ for a horizontal vessel along the X axis, $\Theta=90$ for a vertical vessel along the Z axis) as shown in image, 411. For a given position (Z), the processor also calculates the minimum $\Theta$ for the detected edges and uses this value as representing vessel orientation for a local table position. The processor identifies and uses the most oblique edge for determining table velocity because this is a limiting orientation (i.e. the more oblique an angle the slower the table velocity). The image data processor determines vessel size by image data measurement, performs diameter measurement of a detected vessel orthogonal to a vessel image acquisition plane and examines a vessel for stenosis. The processor quantifies the extent vessel narrowing using detected vessel edges and diameter.

Figure 5:
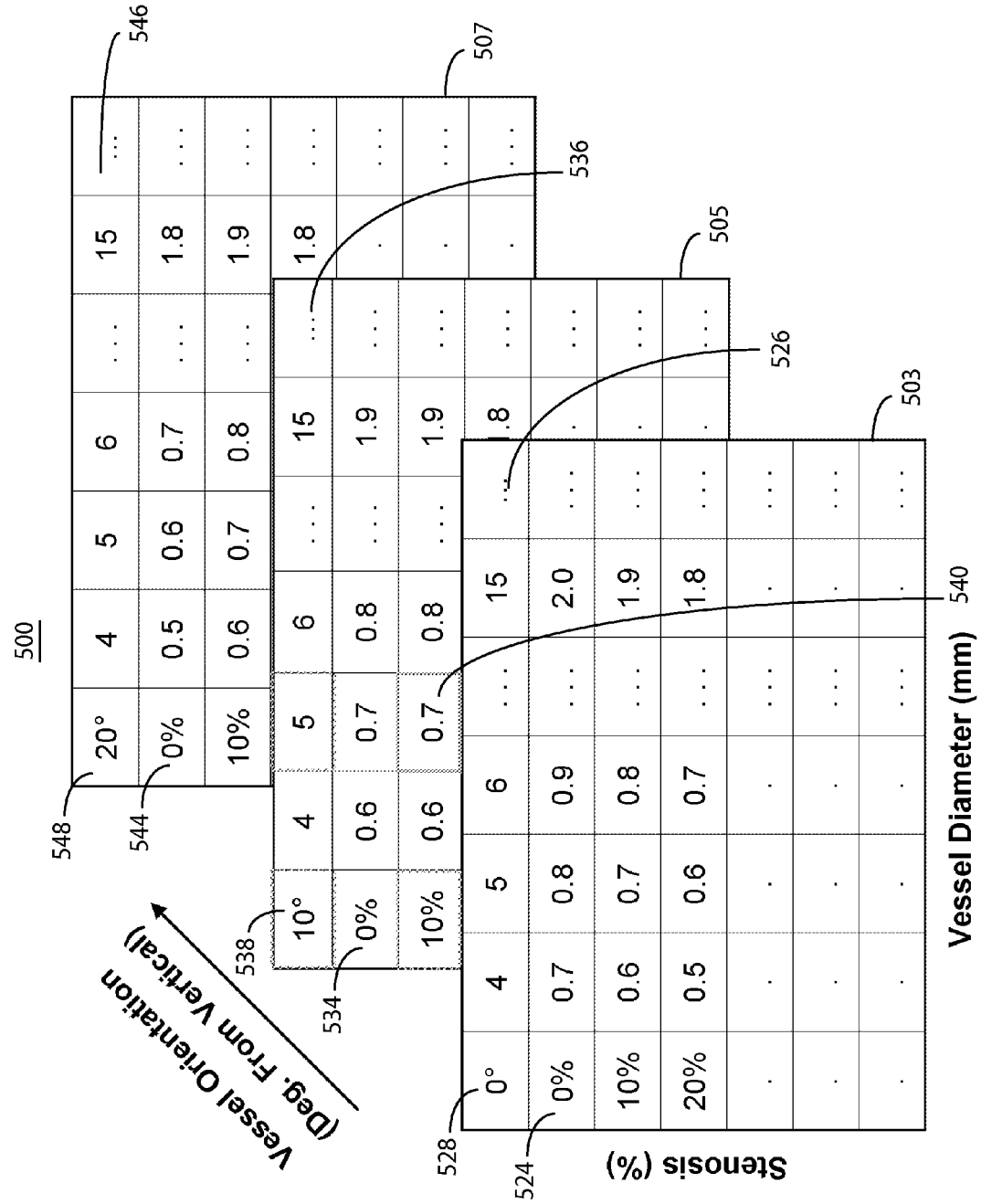
FIG. 5 shows a lookup table, associating multiple values or value ranges of anatomical characteristics of anatomical features (vessel stenosis, diameter and orientation) with table velocity modification data, according to invention principles.

FIG. 5 shows lookup table 500, associating multiple values or value ranges of anatomical characteristics of anatomical features (vessel stenosis, diameter and orientation) with table velocity modification data. A patient support table controller automatically moves patient table 5 (FIG. 1) at a velocity adaptively and dynamically determined by selecting variable (orientation, size and stenosis) data modifying table velocity from predetermined information associating an anatomical feature with table velocity modification data in response to detection of an anatomical feature. Based on determined variables orientation, size and stenosis, the controller utilizes multi-parameter look-up table 500 to calculate change in patient support table 5 velocity. Modified table velocity $V(z)^+$ is adjusted based on previous table velocity $V(z)^-$ and look-up table proportion (P), $$V(z)^+ = P \cdot V(z)^-$$

with P determined from multi-parameter look-up table 500. Table 500 includes individual tables 503 (for zero degrees vessel orientation 528), 505 (for ten degrees vessel orientation 538) and 507 (for 20 degrees vessel orientation 548) for example. The individual tables 503, 505 and 507 includes patient support table velocity modification data P for different combinations of stenosis (%) having values shown in columns 524, 534, 544 and vessel diameter having values shown in rows 526, 536 546 for particular vessel orientation values 528, 538 and 548 respectively.

The patient support table controller uses a single or multi-dimensional look-up table to extract table velocity modification data. Specifically, in an embodiment the controller uses Table 500 to find a patient support table velocity modification data P value for a particular set of stenosis (%), vessel diameter and vessel orientation values that are determined by the image data processor from automatic image analysis. In this embodiment, the system optimizes table velocity when stenosis, vessel orientation, and diameter are considered. For example, for a 5 mm vessel oriented 10° from the vertical line with 10% stenosis, the multi-parameter look-up table would extract P=0.7 (540). Further, if $V(z)^-$ is 3 mm/s, $V(z)^+$ is calculated to be 2.1 mm/s (0.7*3 mm/s). The reduced table velocity takes into account the cumulative challenges of imaging narrow vessels that are not orthogonal to the imaging plane and further exacerbated by stenosis.

While this example relies upon the confluence of several parameters indicating an optimal table velocity, the controller in another embodiment may use other imaged features and a different look-up table. FIG. 6 shows a further lookup table 603, associating multiple values of severity (very significant, significant, moderate, slight—row 605) of anatomical characteristics of anatomical features (flow reduction, artifact, heart deformation, tumor, external device identified in column 607) with table velocity modification data. For instance, if each feature is classified by severity, two-dimensional look-up table 603 is used. In this example, if an artifact is detected and deemed moderate, table velocity is modified using P=0.8 (609).

Figure 7:
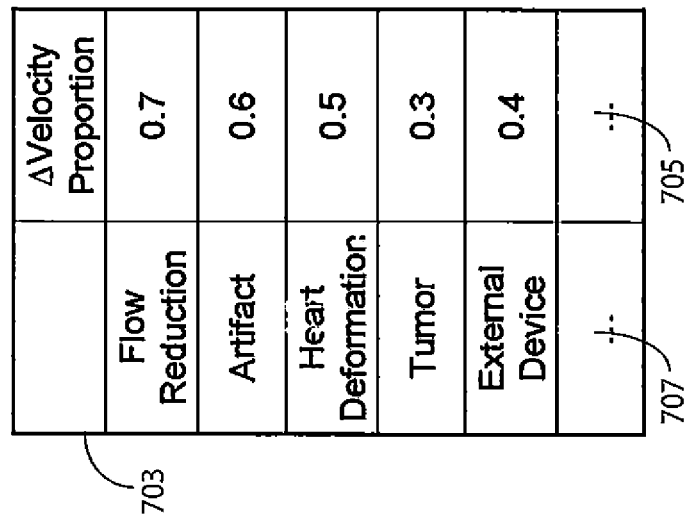
FIG. 7 shows a further lookup table, associating anatomical characteristics of anatomical features (flow reduction, artifact, heart deformation, tumor, external device) with table velocity modification data, according to invention principles.

FIG. 7 shows lookup table 703, associating anatomical characteristics of anatomical features (flow reduction, artifact, heart deformation, tumor, external device identified in column 707) with table velocity modification data (column 705). This lookup table is used to change patient support table velocity in response to a feature in an acquired image (irrespective of severity or extent of the feature): In an example, if $V(z)^-$ is 7 mm/s and a tumor is detected, $V(z)^+$ is adaptively changed to 2.1 mm/s (0.3*7 mm/s).

The image data processor determines flow reduction (FR) in conjunction with functional flow measurements in a flow dependent imaging sequence. The image data processor detects a vessel as described previously. The processor further determines normal blood flow value by determining a running average of signal intensity (higher signal=more inflow) in a vessel. Alternatively, the processor determines a normal blood flow value using a look-up table incorporating patient demographics (age, gender, height, weight, pregnancy status) and corresponding patient population specific imaging parameters. The processor determines blood flow reduction (FR) in a vessel as comprising image intensity of flow in a small sub-region or slice divided by a normal flow value. Modified patient support table velocity $V(z)^+$ is linearly related to previous table velocity $V(z)^-$. Therefore, $V(z)^-$ is multiplied by FR and an additional constant (C) (derived using previously determined empirical data) to give, $$V(z)^+ = C \cdot FR \cdot V(z)^-$$

In a further embodiment, the image data processor selects a template image specific to an imaging region of interest from a data base. The processor performs a non-rigid registration of an imaging volume to the selected template image and quantizes deformation based on scaling parameters used in the non-rigid registration. The patient support table controller modifies table velocity based on a look-up table of table velocity modification data values for a detected scaling value and patient demographic data value set.

Returning to FIG. 1, in the basic magnetic field 1, a cylinder-shaped gradient coil system 3 is used, which consists of three windings, for example. Each winding is supplied with current by an amplifier 14 in order to generate a linear gradient field in the respective directions of the Cartesian coordinate system. The first winding of the gradient field system 3 generates a gradient $G_x$ in the x-direction, the second winding generates a gradient $G_y$ in the y-direction, and the third winding generates a gradient $G_z$ in the z-direction. Each amplifier 14 contains a digital-analog converter, which is controlled by a sequence controller 18 for the generation of gradient pulses at proper times.

Within the gradient field system 3, radio-frequency (RF) coils 4 are located which converts the radio-frequency pulses emitted by a radio-frequency power amplifier 16 via multiplexer 6 into a magnetic alternating field in order to excite the nuclei and align the nuclear spins of the object to be examined or the region of the object to be examined. In one embodiment, RF coils 4 comprise a subset or substantially all of, multiple RF coils arranged in sections along the length of volume M corresponding to the length of a patient. Further, an individual section RF coil of coils 4 comprises multiple RF coils providing RF image data that is used in parallel to generate a single MR image. RF pulse signals are applied to RF coils 4, which in response produces magnetic field pulses which rotate the spins of the protons in the imaged body by ninety degrees or by one hundred and eighty degrees for so-called "spin echo" imaging, or by angles less than or equal to 90 degrees for so-called "gradient echo" imaging. In response to the applied RF pulse signals, RF coils 4 receive MR signals, i.e., signals from the excited protons within the body as they return to an equilibrium position established by the static and gradient magnetic fields. The MR signals comprising nuclear spin echo signals received by RF coils 4 as an alternating field resulting from the precessing nuclear spins, are converted into a voltage that is supplied via an amplifier 7 and multiplexer 6 to a radio-frequency receiver processing unit 8 of a radio-frequency system 22.

The radio-frequency system 22 operates in an RF signal transmission mode to excite protons and in a receiving mode to process resulting RF echo signals. In transmission mode, system 22 transmits RF pulses via transmission channel 9 to initiate nuclear magnetic resonance in volume M. Specifically, system 22 processes respective RF echo pulses associated with a pulse sequence used by system computer 20 in conjunction with sequence controller 18 to provide a digitally represented numerical sequence of complex numbers. This numerical sequence is supplied as real and imaginary parts via digital-analog converter 12 in the high-frequency system 22 and from there to a transmission channel 9. In the transmission channel 9, the pulse sequences are modulated with a radio-frequency carrier signal, having a base frequency corresponding to the resonance frequency of the nuclear spins in the measurement volume M. The conversion from transmitting to receiving operation is done via a multiplexer 6. RF coils 4 emit RF pulses to excite nuclear proton spins in measurement volume M and acquire resultant RF echo signals. The correspondingly obtained magnetic resonance signals are demodulated in receiver processing unit 8 of RF system 22 in a phase-sensitive manner, and are converted via respective analog-digital converters 11 into a real part and an imaginary part of the measurement signal and processed by imaging computer 17.

Figure 8:
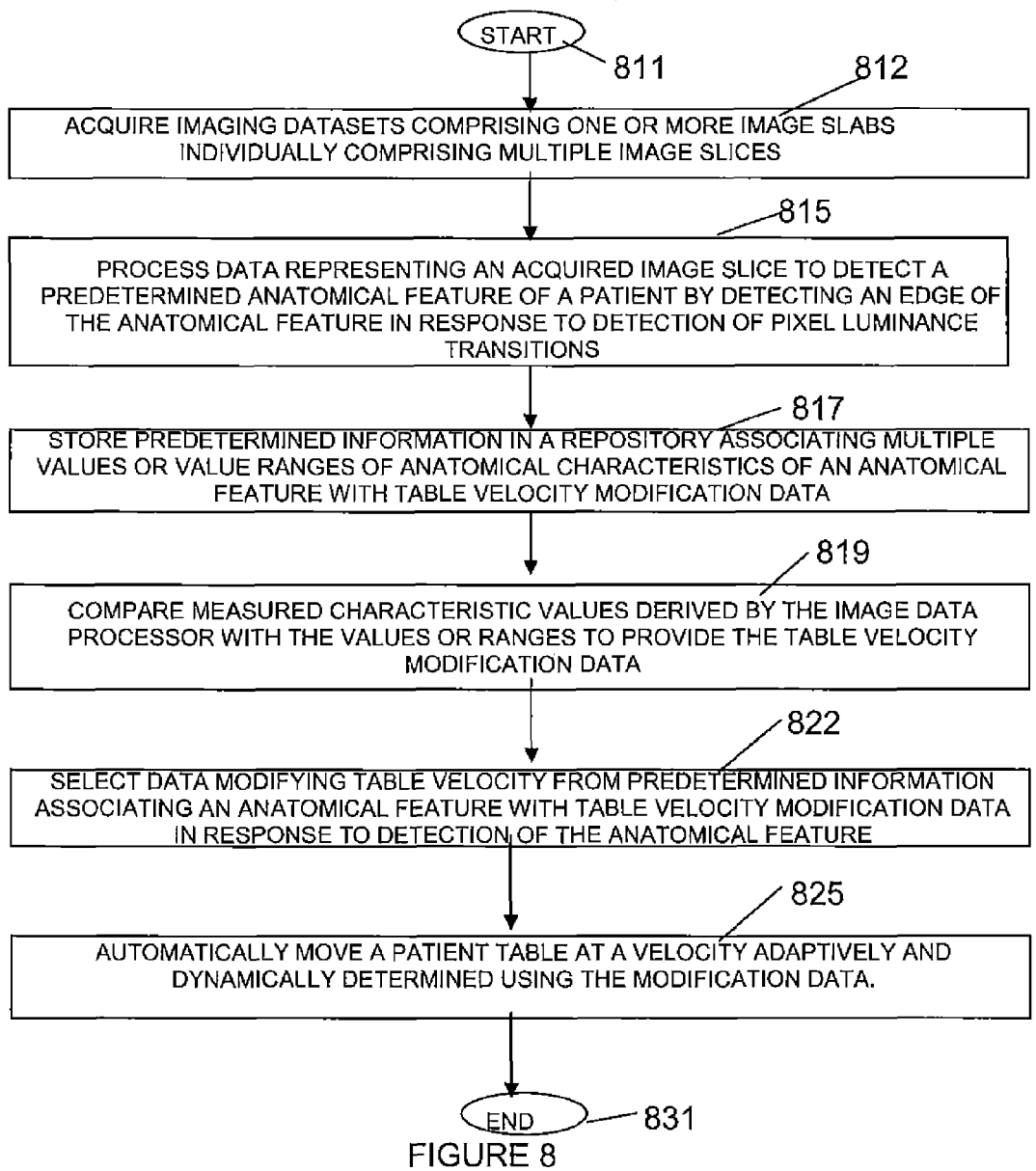
FIG. 8 shows a flowchart of a process performed by a system for Non-Contrast Agent enhanced MR imaging, according to invention principles.

FIG. 8 shows a flowchart of a process performed by system 10 (FIG. 1) for Non-Contrast Agent enhanced MR imaging. In step 812 following the start at step 811, system 10 (including system computer 20 and imaging computer 17) acquires imaging datasets comprising one or more image slabs individually comprising multiple image slices. In step 815 system 10 (an image data processor in system computer 20 or imaging computer 17) processes data representing an acquired image slice to detect a predetermined anatomical feature of a patient by detecting an edge of the anatomical feature in response to detection of pixel luminance transitions. The image data processor detects the predetermined anatomical feature by comparing an individual detected anatomical feature in an image with multiple predetermined template image objects aligning an individual detected anatomical feature in an image with a template image object, scaling at least one of, the individual detected anatomical feature and the template image object and selecting a best match object to identify the individual detected anatomical feature.

The predetermined anatomical feature comprises at least one of, (a) a vessel characteristic, (b) an organ or tissue characteristic associated with a medical condition, (c) a blood flow characteristic, (d) an invasive medical device, (e) degree of stenosis, (f) vessel diameter and (g) angular vessel orientation. Computer 20 in step 817 stores in a repository in computer 20, predetermined information associating multiple values or value ranges of anatomical characteristics of an anatomical feature with table velocity modification data and with particular patient demographic characteristics (including age, weight, gender and height). The table velocity modification data comprises at least one of, (a) a factor used for modifying an existing table velocity and (b) a table velocity.

In step 819, a comparator in the patient support table controller in system 20 compares measured characteristic values derived by the image data processor in computer 20 with the values or ranges to provide the table velocity modification data. In step 822 the patient support table controller selects data modifying table velocity from predetermined information associating one or more anatomical features with table velocity modification data in response to detection of the anatomical feature and patient demographic data including at least one of, age weight, gender and height. In one embodiment, the predetermined information associates multiple anatomical characteristics of an anatomical feature with table velocity modification data and the controller selects data modifying table velocity in response to detection of the multiple anatomical characteristics. The activity of selecting data modifying table velocity comprises selecting data modifying table velocity from predetermined information associating an anatomical feature indicating an impairment and severity of the impairment with table velocity modification.

In step 825 the patient support table controller automatically moves a patient table at a velocity adaptively and dynamically determined using the modification data. In one embodiment the patient support table controller adaptively determines a table velocity using the table velocity modification data in accordance with a function substantially of the form $$V(z)^+ = P \cdot V(z)^-$$

where $V(z)^+$ is an adjusted table velocity, $V(z)^-$ is a previous table velocity and P is modification data. In another embodiment the patient support table controller adaptively determines a patient table velocity using the table velocity modification data in accordance with a function substantially of the form $$V(z)^+ = C \cdot FR \cdot V(z)^-$$

where $V(z)^+$ is an adjusted table velocity, $V(z)^-$ is a previous table velocity, C is a constant, FR is a vessel blood flow reduction factor and P is modification data. The process of FIG. 8 terminates at step 831.

A processor as used herein is a device for executing machine-readable instructions stored on a computer readable medium, for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a computer, controller or microprocessor, for example, and is conditioned using executable instructions to perform special purpose functions not performed by a general purpose computer. A processor may be coupled (electrically and/or as comprising executable components) with any other processor enabling interaction and/or communication therebetween. A user interface processor or generator is a known element comprising electronic circuitry or software or a combination of both for generating display images or portions thereof. A user interface comprises one or more display images enabling user interaction with a processor or other device.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A user interface (UI), as used herein, comprises one or more display images, generated by a user interface processor and enabling user interaction with a processor or other device and associated data acquisition and processing functions.

The UI also includes an executable procedure or executable application. The executable procedure or executable application conditions the user interface processor to generate signals representing the UI display images. These signals are supplied to a display device which displays the image for viewing by the user. The executable procedure or executable application further receives signals from user input devices, such as a keyboard, mouth, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity.

The system and processes of FIGS. 1-8 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. A system varies table speed during continuous table movement magnetic resonance imaging (MRI) based on imaging features detected from a previous scan, imaging features detected during a current scan and use of anatomical region-specific table speed. Further, the system and processes may, in alternative embodiments, be located on one or more (e.g., distributed) processing devices on a network linking the units of FIG. 1. Any of the functions and steps provided in FIGS. 1-8 may be implemented in hardware, software or a combination of both.

What is claimed is:

1. A system for Non-Contrast Agent enhanced MR imaging, comprising:
    an MR image acquisition device for acquiring imaging datasets of a patient comprising one or more image slabs individually comprising a plurality of image slices;
    an image data processor for processing data representing an acquired image slice to detect an anatomical feature of said patient by detecting an edge of said anatomical feature in response to detection of pixel luminance transitions; and
    a patient support table controller for automatically moving a patient table at a velocity adaptively and dynamically determined by,
    selecting a table velocity modification parameter from a plurality of table velocity modification parameters using predetermined information associating a plurality of anatomical characteristics of said anatomical feature with said plurality of table velocity modification parameters in response to detection of said anatomical feature in said acquired image slice of said patient, each of said plurality of anatomical characteristics being associated with one of said plurality of table velocity modification parameters, and
    adaptively determining a table velocity using the selected table velocity modification parameter.

2. A system according to claim 1, wherein said image slice of said patient is acquired from at least one of, (a) a previous scan of said patient and (b) a current image acquisition scan of said patient.

3. A system according to claim 2, wherein said plurality of anatomical characteristics of said anatomical feature comprise at least two of (a) degree of stenosis, (b) vessel diameter and (c) angular vessel orientation.

4. A system according to claim 1, including
    a repository of predetermined information, associating a plurality of values or value ranges of said anatomical characteristics of said anatomical feature with said plurality of table velocity modification parameters and including
    a comparator for comparing measured characteristic values derived by said image data processor with said values or ranges to provide the plurality of said table velocity modification parameters.

5. A system according to claim 4, wherein said predetermined information associates ranges of characteristic values with particular patient demographic characteristics and said system uses patient demographic data including at least one of, age weight, gender and height in determining said plurality of table velocity modification parameters.

6. A system according to claim 1, wherein said image data processor detects said detected anatomical feature by
    comparing said detected anatomical feature in an image with a plurality of predetermined template image objects,
    selecting a best match object to identify said detected anatomical feature.

7. A system according to claim 6, wherein said image data processor detects said detected anatomical feature by aligning said detected anatomical feature in an image with a template image object.

8. A system according to claim 7, wherein said image data processor detects said detected anatomical feature by scaling at least one of, said detected anatomical feature and said template image object.

9. A system according to claim 1, wherein said detected anatomical feature comprises at least one of, (a) a vessel characteristic, (b) an organ or tissue characteristic associated with a medical condition, (c) a blood flow characteristic and (d) an invasive medical device.

10. A method employed by a system for Non-Contrast Agent enhanced MR imaging, comprising the activities of:
    acquiring imaging datasets of a patient comprising one or more image slabs individually comprising a plurality of image slices;
    processing data representing an acquired image slice to detect an anatomical feature of said patient by detecting an edge of said anatomical feature in response to detection of pixel luminance transitions; and
    automatically moving a patient table at a velocity adaptively and dynamically determined by,
    selecting a table velocity modification parameter from a plurality of table velocity modification parameters using predetermined information associating a plurality of anatomical characteristics of said anatomical feature with said plurality of table velocity modification parameters in response to detection of said anatomical feature in said acquired image slice of said patient, each of said plurality of anatomical characteristics being associated with one of said plurality of table velocity modification parameters, and
    adaptively determining a table velocity using the selected table velocity modification parameters.

11. A method according to claim 10, wherein said image slice of said patient is acquired from at least one of, (a) a previous scan of said patient and (b) a current image acquisition scan of said patient.

12. A method according to claim 11, wherein said plurality of anatomical characteristics of said anatomical feature comprise at least two of, (a) degree of stenosis, (b) vessel diameter and (c) angular vessel orientation and including the activity of adaptively determining a table velocity using the selected table velocity modification parameter in accordance with a function substantially of the form $$V(z)^+ = P \cdot V(z)^-$$

Where $V(z)^+$ is an adjusted table velocity, $V(z)^-$ is a previous table velocity and P is said selected modification parameter.

13. A method according to claim 10, wherein including the activity of adaptively determining a table velocity using the table velocity modification data in accordance with a function substantially of the form $$V(z)^+ = C \cdot FR \cdot V(z)^-$$

where $V(z)^+$ is an adjusted table velocity, $V(z)^-$ is a previous table velocity, C is a constant, FR is a vessel blood flow reduction factor and P is said selected modification parameter.

14. A method according to claim 10, wherein said activity of selecting said table velocity modification parameter comprises using predetermined information associating said anatomical feature indicating an impairment and severity of said impairment with table velocity modification.

15. A method according to claim 10, wherein said activity of selecting said table velocity modification parameter comprises using predetermined information associating said anatomical feature indicating an impairment with table velocity modification.

16. A method according to claim 10, including the activities of
storing said predetermined information in a repository associating a plurality of values or value ranges of said plurality of anatomical characteristics of said anatomical feature with said plurality of table velocity modification parameters and including the activity of
comparing measured characteristic values derived by said image data processor with said plurality of values or ranges to provide the selected table velocity modification parameter.

17. A method according to claim 16, wherein said predetermined information associates ranges of characteristic values with particular patient demographic characteristics and said method uses patient demographic data including at least one of, age weight, gender and height in selecting said table velocity modification parameter.

18. A method according to claim 10, including the activity of detecting said anatomical feature by comparing said detected anatomical feature in said acquired image with a plurality of predetermined template image objects, aligning said detected anatomical feature in said image with a template image object of said plurality of predetermined template image objects and selecting a best match object to identify said detected-anatomical feature.

19. A method according to claim 18, including the activity of
detecting said anatomical feature by scaling at least one of, said detected anatomical feature and said template image object and
said detected anatomical feature comprises at least one of (a) a vessel characteristic, (b) an organ or tissue characteristic associated with a medical condition, (c) a blood flow characteristic and (d) an invasive medical device.

20. A system for Non-Contrast Agent enhanced MR imaging, comprising:
an MR image acquisition device for acquiring imaging datasets of a patient comprising one or more image slabs individually comprising a plurality of image slices;
an image data processor for processing data representing an acquired image slice to detect an anatomical feature of said patient by detecting an edge of said anatomical feature in response to detection of pixel luminance transitions; and
a patient support table controller for automatically moving a patient table at a velocity adaptively and dynamically determined by,
selecting, in response to detection of said anatomical feature in said acquired image slice of said patient, a table velocity modification parameter from a plurality of table velocity modification parameters using predetermined information associating each one of a plurality of anatomical features with one of said table velocity modification parameters, and
adaptively determining a table velocity using the selected table velocity modification parameter.

* * * * *